United States Patent
Wang et al.

(10) Patent No.: US 9,314,161 B2
(45) Date of Patent: Apr. 19, 2016

(54) MOVING OBJECT CONTOUR EXTRACTION APPARATUS, LEFT VENTRICLE IMAGE SEGMENTATION APPARATUS, MOVING OBJECT CONTOUR EXTRACTION METHOD AND LEFT VENTRICLE IMAGE SEGMENTATION METHOD

(75) Inventors: Yanhua Wang, Beijing (CN); Chao Cong, Beijing (CN); Yanli Wang, Beijing (CN); Shaobin Wang, Beijing (CN)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 820 days.

(21) Appl. No.: 13/553,022

(22) Filed: Jul. 19, 2012

(65) Prior Publication Data
US 2013/0184570 A1 Jul. 18, 2013

(30) Foreign Application Priority Data
Jul. 19, 2011 (CN) .......................... 2011 1 0209867

(51) Int. Cl.
| | |
|---|---|
| G06K 9/00 | (2006.01) |
| A61B 5/00 | (2006.01) |
| G06T 7/00 | (2006.01) |
| G06T 7/20 | (2006.01) |
| G06T 7/60 | (2006.01) |
| A61B 5/055 | (2006.01) |
| A61B 6/03 | (2006.01) |
| A61B 6/00 | (2006.01) |
| A61B 8/08 | (2006.01) |
| A61B 8/13 | (2006.01) |

(52) U.S. Cl.
CPC ............. *A61B 5/0073* (2013.01); *A61B 5/0044* (2013.01); *A61B 5/055* (2013.01); *A61B 6/032* (2013.01); *A61B 6/037* (2013.01); *A61B 6/503* (2013.01); *A61B 8/0883* (2013.01); *A61B 8/13* (2013.01); *G06T 7/0083* (2013.01); *G06T 7/2033* (2013.01); *G06T 7/602* (2013.01); *G06T 2207/30048* (2013.01)

(58) Field of Classification Search
None
See application file for complete search history.

(56) References Cited

U.S. PATENT DOCUMENTS

| | | | |
|---|---|---|---|
| 5,570,430 A | 10/1996 | Sheehan et al. | |
| 6,728,566 B1 * | 4/2004 | Subramanyan | ....... G06T 11/005 600/407 |

(Continued)

FOREIGN PATENT DOCUMENTS

DE    10 2008 008 601 A1    8/2009

OTHER PUBLICATIONS

Extended European Search Report issued Mar. 28, 2013 in Patent Application No. 12177159.6.

(Continued)

*Primary Examiner* — Nancy Bitar
(74) *Attorney, Agent, or Firm* — Oblon, McClelland, Maier & Neustadt, L.L.P

(57) ABSTRACT

According to one embodiment, a moving object contour extraction apparatus includes a contour acquisition unit and a contour correction unit. The contour acquisition unit is configured to acquire a contour of a moving object in each image slice. The contour correction unit is configured to correct the contours of the moving object in image slices of at least one image slice time series based on motion trend information of the moving object in each of a plurality of image slice time series.

11 Claims, 15 Drawing Sheets

(56) References Cited

U.S. PATENT DOCUMENTS

| | | | | |
|---|---|---|---|---|
| 2003/0153823 | A1* | 8/2003 | Geiser | G06T 7/0012 600/407 |
| 2008/0304730 | A1* | 12/2008 | Abe | A61B 8/08 382/131 |
| 2009/0131788 | A1* | 5/2009 | Settlemier | A61B 8/0858 600/438 |
| 2009/0214090 | A1 | 8/2009 | Hayes | |
| 2009/0232371 | A1* | 9/2009 | Jolly | G06K 9/342 382/128 |
| 2009/0290777 | A1 | 11/2009 | Sun et al. | |
| 2010/0145197 | A1* | 6/2010 | Stapf | A61B 5/416 600/445 |
| 2010/0215238 | A1 | 8/2010 | Lu et al. | |
| 2011/0019934 | A1* | 1/2011 | Ledinh | H04N 19/176 382/261 |
| 2012/0078097 | A1* | 3/2012 | Wang | G06T 7/2046 600/437 |
| 2013/0182935 | A1* | 7/2013 | Wang | G06T 7/2033 382/133 |

OTHER PUBLICATIONS

Uday Kurkure, et al. "Localization and Segmentation of Left Ventricle in Cardiac Cine-MR Images", IEEE Transactions on Biomedical Engineering, XP011342944A, vol. 56, No. 5, May 2009, pp. 1360-1370.

Hae-Yeoun Lee, et al., "Automatic left Ventricle Segmentation Using Iterative Thresholding and an Active Contour Model with Adaptation on Short-Axis Cardiac MRI", IEEE Transactions on Biomedical Engineering, XP011343198A, vol. 57, No. 4, Apr. 2010, pp. 905-913.

Partial European Search Report Issued Nov. 16, 2012 in Patent Application No. 12177159.6.

Cristiana Corsi et al., "1097 Automated frame-by-frame endocardial border detection from cardiac magnetic resonance images for quantitative assessment of left ventricular function: validation and clinical feasibility", Journal of Cardiovascular Magnetic Resonance, XP021044211, vol. 10, Oct. 22, 2008, 2 pages.

Patrice Lilly et al. "Automatic Contour Definition on Left Ventriculograms by Image Evidence and a Multiple Template-Based Model", IEEE Transactions on medical Imaging, XP000097205, vol. 8, No. 2, Jun. 1989, pp. 173-185.

* cited by examiner

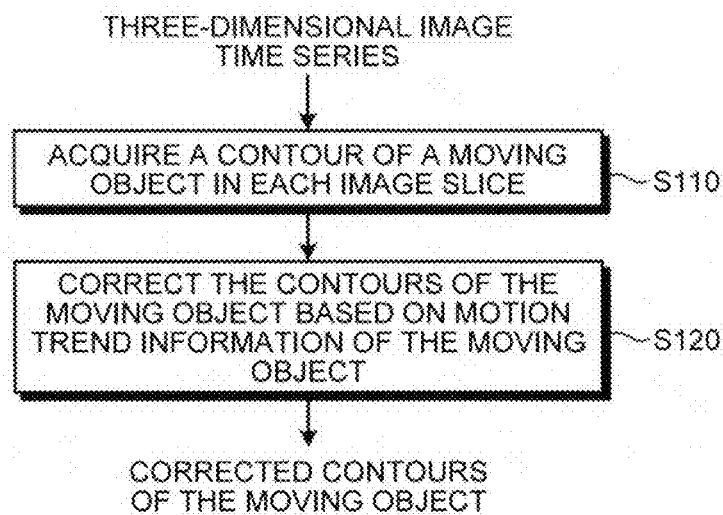
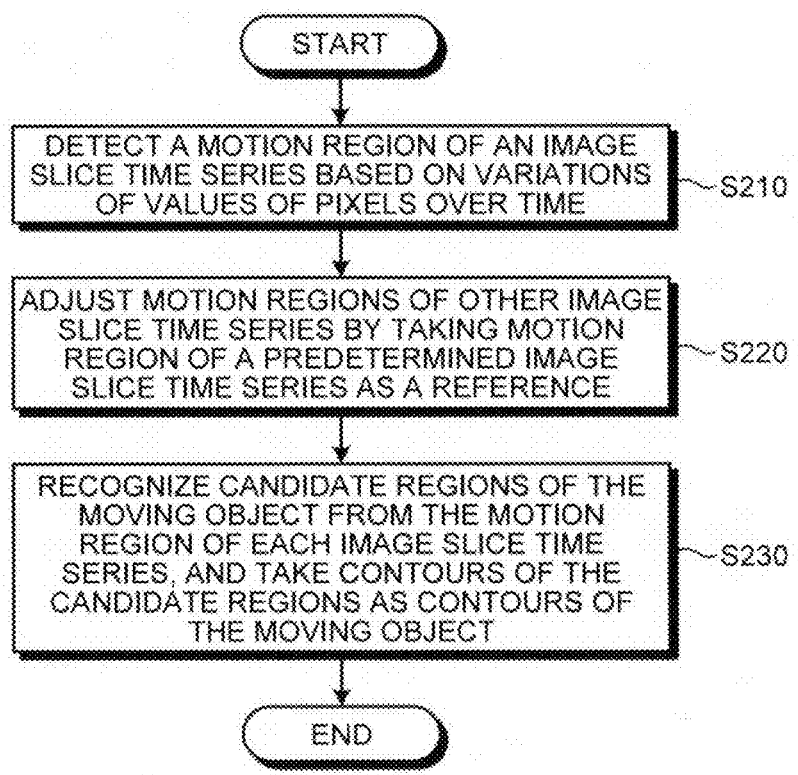

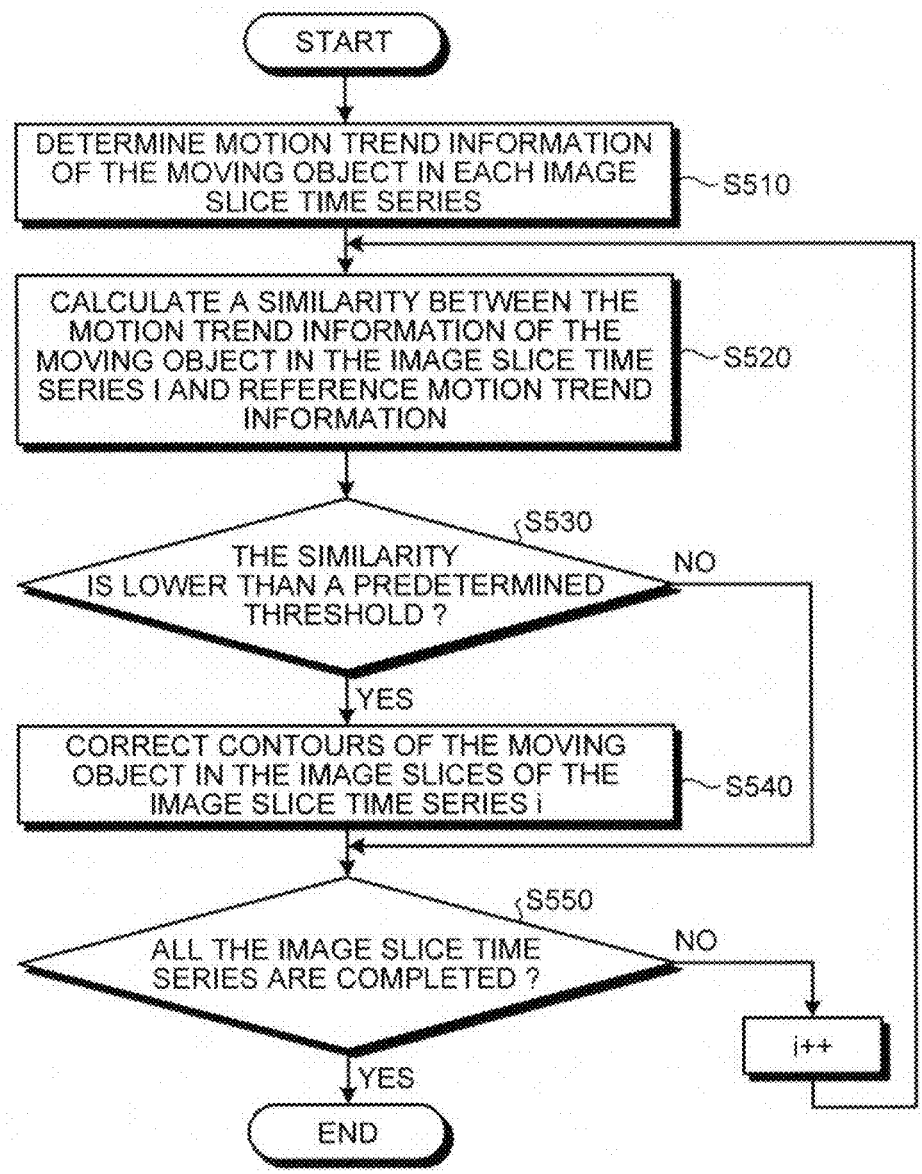

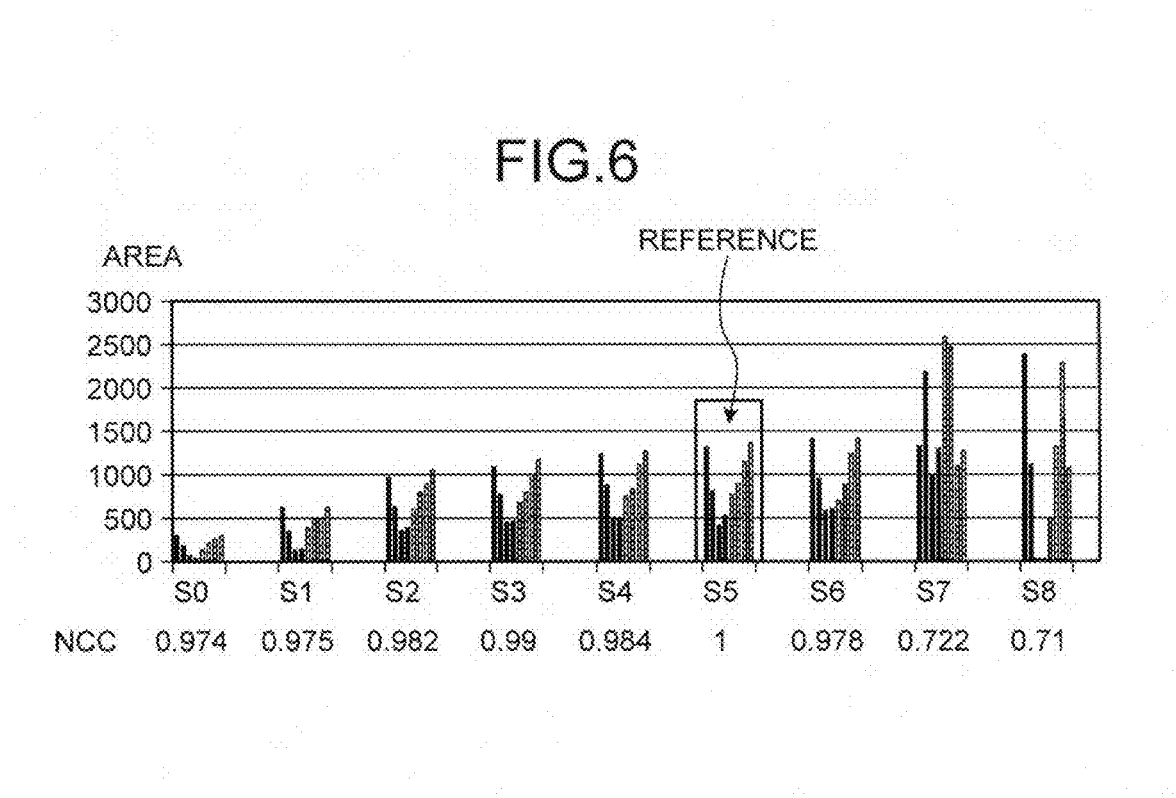

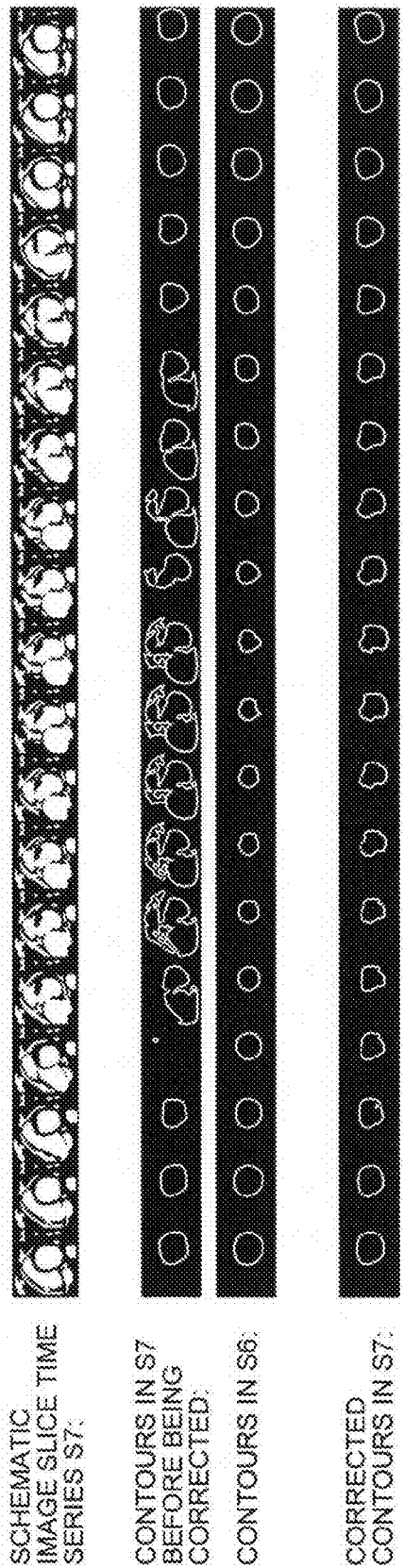

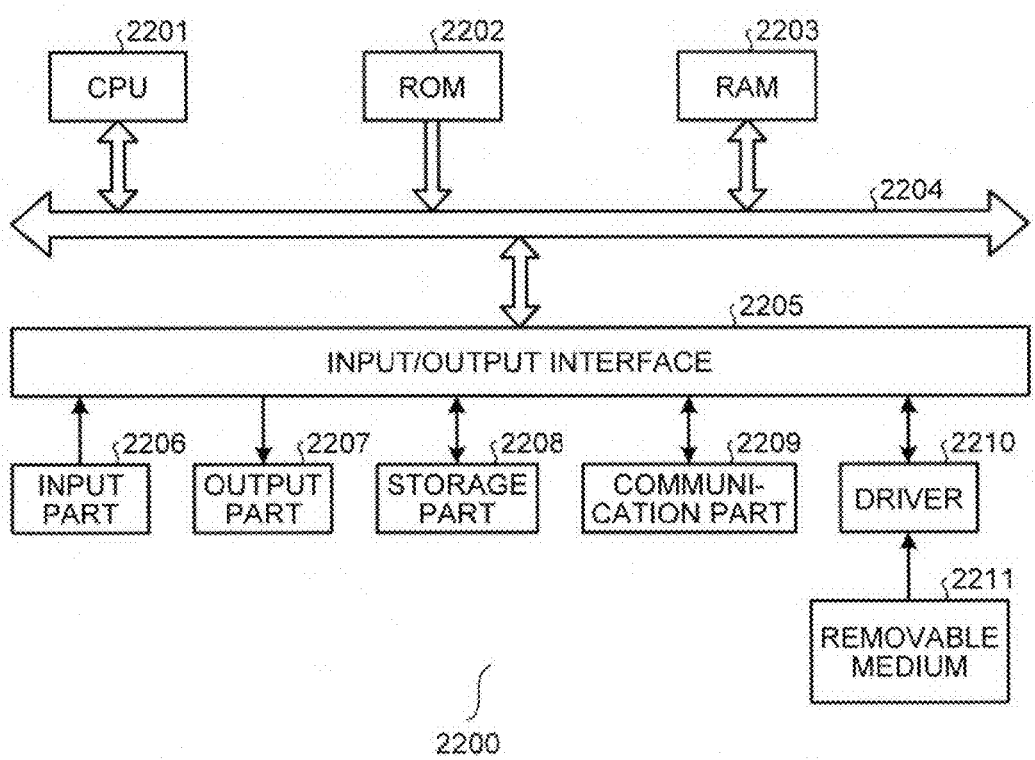

US 9,314,161 B2

MOVING OBJECT CONTOUR EXTRACTION APPARATUS, LEFT VENTRICLE IMAGE SEGMENTATION APPARATUS, MOVING OBJECT CONTOUR EXTRACTION METHOD AND LEFT VENTRICLE IMAGE SEGMENTATION METHOD

CROSS-REFERENCE TO RELATED APPLICATIONS

This application is based upon and claims the benefit of priority from Chinese Patent Application No. 201110209867.4, filed on Jul. 19, 2011, the entire contents of which are incorporated herein by reference.

FIELD

Embodiments described herein relate generally to a moving object contour extraction apparatus, a left ventricle image segmentation apparatus, a moving object contour extraction method and a left ventricle image segmentation method

BACKGROUND

The contour extraction of a moving object, especially of a deforming object, is a challenge in the field of computer vision. In actual applications, for example, in the medical field, the contour extraction of an organ or a part of an organ from a three-dimensional image time series acquired by a computed tomography (CT) apparatus, a Magnetic Resonance Imaging (MRI) apparatus, an ultrasonic (UL) apparatus and the like is beneficial to subsequent measurement on various parameters of the organ. However, the deforming motion of an object leads to a large variation in the orientation, size and shape of the object in an image time series and the image intensity, thus it is difficult to accurately extract the contours of the object in the respective images at different motion stages.

In addition, in the field of cardiology, a nuclear magnetic resonance imaging technology is typically used to provide a three-dimensional image time series (3D+T) of a heart. Doctors are highly interested in recognizing a ventricle, an endocardium, an epicardium. The contours of the recognized ventricle, endocardium and epicardium can be used to measure a ventricular blood volume (ejection fraction), the motion of a ventricular wall, a feature of wall thickness and the like at different stages of a cardiac cycle. The left ventricle (LV) is of great importance because it pumps oxygenated blood to various issues of a body from the heart.

In the prior art, models, some researchers have constructed models such as a four-dimensional (4D) probabilistic atlas of a heart and a three-dimensional (3D) LV surface model to aid left ventricle segmentation. Also some methods are studied to segment LV using an active shape by gradient, intensity and shape features. Certainly, more semi-automatic LV segmentation methods are studied which make use of user interaction. In recent years, more and more researchers have been devoted to the development of a fully-automatic LV segmentation method and made some achievements. For instance, Marie-Pierre Jolly and Ying Sun respectively proposed some methods (referring to US Patent Applications US2009/0232371 and US2009/0290777) as to the automatic segmentation of an LV.

The model-based methods provided in the prior art have difficulties in capturing variations beyond the training sets thereof. The commonly-used methods based on snake (dynamic contour model) algorithm are quite sensitive to noises and physical papillary muscle of the LV, and sometimes also sensitive to initial conditions. Most of the semi-automatic methods need the interaction of a user, which is subjective and time-consuming for the doctors. Some automatic methods have many assumptions on the shape and pixel brightness of the heart and need improvement in robustness.

BRIEF DESCRIPTION OF THE DRAWINGS

The present invention can be better understood by reference to the following description taken in conjunction with accompanying drawings. In the drawings, identical or like sections are designated with identical or like reference signs. The accompanying drawings, together with the detailed description below, are incorporated into and form a part of the specification, and serve to further illustrate, by way of example, preferred embodiments of the present invention and to explain the principle and advantages of the present invention. In the accompanying drawings:

FIG. 1 is a schematic flow chart illustrating a moving object contour extraction method according to an embodiment of the present invention;

FIG. 2 is a schematic flow chart illustrating the acquiring of a contour of a moving object in each image slice according to an embodiment of the present invention;

FIG. 5 is a schematic flow chart illustrating the correcting of a contour of a moving object based on motion trend information of the moving object according to an embodiment of the present invention;

FIG. 6 shows an example of motion trends of a moving object in a plurality of image slice time series and similarities between the motion trends of the moving object and a reference motion trend;

FIG. 7 shows an example of the correcting of contours of a moving object in an image slice time series;

FIG. 22 is an exemplary block diagram illustrating a computer structure capable of implementing the methods/apparatuses disclosed in the embodiments of the preset invention.

DETAILED DESCRIPTION

Figure 3:
FIG. 3 shows an example of the adjusting of motion regions of other image slice time series by taking a motion region of a predetermined image slice time series as a reference.

The following presents a simplified summary of the present invention to provide a basic understanding of some aspects of the present invention. It should be understood that the summary is not an exhaustive summary of the present invention. It is not intended to identify the key or critical parts of the present invention, nor intended to limit the scope of the present invention. It only aims to present some concepts in a simplified form as a prelude to the more detailed description that is to be discussed later.

It is an object of the present invention to provide a moving object contour extraction method and apparatus to accurately acquire contours of the moving object in various images at different motion stages. It is another object of the present invention to provide a left ventricle image segmentation method and apparatus to accurately and robustly segment a left ventricle from an image.

According to an aspect of the present invention, there is provided a moving object contour extraction method for extracting from a three-dimensional image time series contours of a moving object which performs a deforming motion, the three-dimensional image time series including a plurality of three-dimensional images acquired at a plurality of time points, each of the three-dimensional images consisting of a plurality of parallel two-dimensional image slices, and the two-dimensional image slices located at the same location in the plurality of three-dimensional images forming an image slice time series. The moving object contour extraction method includes: acquiring a contour of the moving object in each image slice; and correcting the contours of the moving object in the image slices of at least one image slice time series based on motion trend information of the moving object in each of a plurality of the image slice time series.

According to another aspect of the present invention, there is provided a moving object contour extraction apparatus for extracting from a three-dimensional image time series contours of a moving object which performs a deforming motion, the three-dimensional image time series including a plurality of three-dimensional images acquired at a plurality of time points, each of the three-dimensional images consisting of a plurality of parallel two-dimensional image slices, and the two-dimensional image slices located at the same location in the plurality of three-dimensional images forming an image slice time series. The moving object contour extraction apparatus includes: a contour acquisition unit configured to acquire a contour of the moving object in each image slice; and a contour correction unit configured to correct the contours of the moving object in the image slices of at least one image slice time series based on motion trend information of the moving object in each of a plurality of the image slice time series.

According to still another aspect of the present invention, there is provided a left ventricle image segmentation method for acquiring contours of a left ventricle from a three-dimensional medical image time series, the three-dimensional medical image time series including a plurality of three-dimensional images acquired at a plurality of time points in a period including at least one cardiac cycle, each of the three-dimensional images consisting of a plurality of parallel two-dimensional image slices that are intersected with a long axis of the left ventricle, and the two-dimensional image slices located at the same location in the plurality of three-dimensional images forming an image slice time series. The left ventricle image segmentation method includes: acquiring a pole in each image slice for polar coordinate conversion; converting each image slice into a polar coordinate system based on the pole in the image slice; acquiring, in the polar coordinate system, an endocardial contour of the left ventricle in each image slice as a contour of the left ventricle in the image slice; and mapping the contour of the left ventricle acquired in the polar coordinate system to a corresponding original image slice.

According to still another aspect of the present invention, there is provided a left ventricle image segmentation apparatus for acquire contours of a left ventricle from a three-dimensional medical image time series, the three-dimensional medical image time series including a plurality of three-dimensional images acquired at a plurality of time points in a period including at least one cardiac cycle, each of the three-dimensional images consisting of a plurality of parallel two-dimensional image slices that are intersected with a long axis of the left ventricle, and the two-dimensional image slices located at the same location in the plurality of three-dimensional images forming an image slice time series. The left ventricle image segmentation apparatus includes: a pole acquisition unit configured to acquire a pole in each image slice for polar coordinate conversion; a coordinate conversion unit configured to convert each image slice into a polar coordinate system based on the pole in the image slice; and an endocardial contour acquisition unit configured to acquire, in the polar coordinate system, an endocardial contour of the left ventricle in each image slice as a contour of the left ventricle in the image slice; and the coordinate conversion unit is configured to map the contour of the left ventricle acquired by the endocardial contour acquisition unit in the polar coordinate system to a corresponding original image slice.

Moreover, according to yet another aspect of the present invention there is provided a computer program for realizing the foregoing methods.

Additionally, according to still another aspect of the present invention, there is provided a computer program product, which is in the form of at least a computer readable medium, and on which computer program codes for realizing the foregoing methods are recorded.

Embodiments of the present invention are described below with reference to the accompanying drawings. The elements and features described in a figure or an embodiment of the present invention can be combined with elements and features shown in one or more other figures or embodiments. It should be noted that, for the purpose of clarity, representations and descriptions of components and processes which are known to those skilled in the art or are not related to the present invention are not presented in the drawings and the description.

Exemplary embodiments of the present invention are described below in the following order:
1. A moving object contour extraction method
2. A left ventricle image segmentation method
3. A moving object contour extraction apparatus
4. A left ventricle image segmentation apparatus
5. A computer structure capable of implementing the methods/apparatuses in the preset disclosure <1. A Moving Object Contour Extraction Method>

A moving object contour extraction method according to embodiments of the present invention is described with reference to FIG. 1 to FIG. 7. The moving object contour extraction method according to the embodiments of the present invention is configured to extract contours of a moving object which performs a deforming motion from a three-dimensional image time series. The three-dimensional image time series includes a plurality of three-dimensional images acquired at a plurality of time points. Each of the three-dimensional images consists of a plurality of parallel two-dimensional image slices. The two-dimensional image slices located at the same location in the three-dimensional images form an image slice time series. It should be appreciated that the moving object contour extraction method according to the embodiments of the present invention may be used to extract contours of a moving object from various types of three-dimensional image time series. As an example but not a limitation, the three-dimensional image time series may be a medical image series formed by data on an examinee obtained by a medial diagnostic imaging device. The medial diagnostic imaging device includes but is not limited to an X-ray imaging diagnostic device, an ultrasonic (UL) diagnostic imaging device, a computed tomography (CT) device, a magnetic resonance imaging (MRI) diagnostic device, a positron emission tomography (PET) device and the like.

FIG. 1 is a schematic flow chart illustrating a moving object contour extraction method according to an embodiment of the present invention. In this embodiment, the deformation of a moving object is turned into a beneficial factor, and a contour of the moving object is corrected with a motion trend of the moving object.

As shown in FIG. 1, in step S110, a contour of a moving object in each image slice is acquired. Here the contour of the moving object may be acquired using any existing method. For example, the contour of the moving object may be acquired by labeling manually. For another example, a candidate region of the moving object may be detected from each image slice using an existing object detection method, and then a contour of the candidate region of the moving object is taken as a contour of the moving object. As a preferred mode proposed in this application, a moving object contour extraction method according to an embodiment of the present invention will be described later in combination with FIG. 2 to FIG. 4.

After acquiring the contours of the moving objection, in step S120, the contours of the moving object are corrected based on motion trend information of the moving object. As the moving object is a whole entity and the deformation motions of the respective parts of the moving object are generally uniform, thus the trend of the deformation motions has consistency. As seen from the sections of the moving object which are parallel to each other, the motions of the sections should be correlated with each other. Therefore, the motion trend of the moving object should be consistent in the image slice time series. Accordingly, the variation trend of the contour of the moving object should also be consistent in the image slice time series. When the motion trend of the moving object in an image slice time series is inconsistent with that of the moving object in most image slice time series or is inconsistent with a reference motion trend, it can be determined that there may be an error in the contours acquired in the image slice time series and these contours need to be corrected such that the motion trend of the moving object in the image slice time series after the correction is consistent with that of the moving object in most image slice time series or is consistent with the reference motion trend. The correction may be carried out by those skilled in the art in various manners under the guide of the foregoing description. As a preferred mode proposed in the present invention, a moving object contour extraction method according to embodiments of the present invention will be described later in combination with FIG. 5 to FIG. 7.

FIG. 2 is a schematic flow chart illustrating the acquiring of a contour of a moving object in each image slice according to an embodiment of the present invention.

In step S210, a motion region of each image slice time series is detected based on variations of the values of pixels in the image slice time series over time. For an image slice time series, the value of each pixel in the motion region of the image slice time series changes significantly over time. There are many methods in the prior art for realizing this step, such as a time-domain variance method, a frame difference method and the like, which are not described here in detail.

In step S220, the motion region of a predetermined image slice time series in the three-dimensional image time series is taken as a reference to adjust the motion regions of other image slice time series in the three-dimensional image time series than the predetermined image slice time series. Typically, in actual applications, the image slice time series in which the moving object suffers interference least may be taken as the predetermined image slice time series. Such an image slice time series may be designated manually or predetermined to be at a location by experience, for example.

In order to facilitate understanding, FIG. 3 shows an example of the adjusting of motion regions of other image slice time series by taking a motion region of a predetermined image slice time series as a reference. In this example, it is shown a schematic diagram of a three-dimensional image time series acquired by an MRI device in a short axis direction of a heart (that is, a direction vertical to a long axis direction of the heart, and generally it may be a direction intersected with the long axis of the heart). It can be known from the motion region detection process in S210 that one image slice time series generally corresponds to one motion region, that is, the image slices in the same image slice time series have the same motion region. For the purpose of concision, each image slice shown in FIG. 3 is a schematic diagram of an optional image slice in an image slice time series. As an example, the moving object shown in FIG. 3 is a left ventricle of a heart, and the image slices shown in FIG. 3 each are a schematic diagram of an image slice in a respective image slice time series acquired in a diastolic period. In FIG. 3, the image slice shown at the top is an image slice of a base part, the image slice shown at the bottom is an image of an apex part, and the image slices between the top and the bottom are orderly arranged image slices of the parts located between the base part and the apex part. It should be noted that a heart image is provided here as an example for describing the moving object contour extraction method and apparatus, but is not to be construed as a limitation to the present invention. On the contrary, the present invention can be applied to any image containing a moving object.

In the example shown in FIG. 3, the motion region of the image slice time series of the base part at the top is taken as a reference to adjust the motion regions of the remaining image slice time series. The solid line frames in the remaining image slice time series represent the adjusted motion regions. The dashed line frame in the image slice of the apex part at the bottom shows the motion region before being adjusted (which is not shown in other image slices).

For the left ventricle in the image slices acquired in the short axis direction of the heart, the major interference source is large blood vessels around the heart. The large blood vessels have a shape similar to that of the left ventricle, and also move. For the reasons such as that the amount of the motion of the apex is relatively small, the apex part tends to be influenced more by the motion of the large blood vessels. Therefore, in the example shown in FIG. 3, the image slice time series of the base part suffering the least interference is taken as the predetermined time series, and the motion regions of the other image slice time series than the image slice time series of the base part are adjusted based on the motion region of the image slice time series of the base part, thereby eliminating the interference caused by the large blood vessels in the other image slice time series.

Returning to FIG. 2, in step S230, candidate regions of the moving object are recognized from the motion region of each image slice time series, and contours of the candidate regions of the moving object are taken as contours of the moving object. The candidate region of the moving object in each image slice can be detected from the motion region of each image slice time series using any appropriate existing object detection method, such as a multiple-feature recognition method.

Figure 4A:
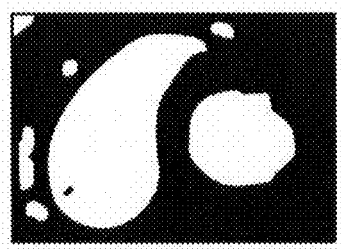
FIG. 4A and FIG. 4B show an example of the recognizing of a candidate region of a moving object from a motion region of an image slice time series.
Figure 4B:
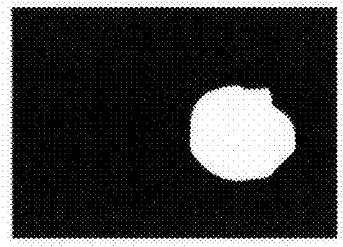

In order to facilitate understanding, FIGS. 4A-4B show an example of the recognizing of a candidate region of a moving object from the motion region of an image slice time series. FIG. 4A shows a motion region of an image slice in a three-dimensional image time series acquired by an MRI device in a short axis direction of the heart, in which the motion region is binarized and connected regions are marked in the motion region. It can be seen from FIG. 4A that the two biggest connected regions are the candidate region of the left ventricle and the candidate region of the right ventricle respectively. FIG. 4B shows a binary image of the motion region of the left ventricle, in which the connected region is the recognized candidate region of the left ventricle. In FIG. 4B, the contour of the recognized candidate region of the left ventricle can be taken as the contour of the left ventricle.

Besides, according to an embodiment of the present invention, the predetermined image slice time series can be determined according to a feature extracted from the motion region of each image slice time series. As an example but not a limitation, the feature may be at least one of the following features: an average pixel value, a ratio of a white connected region in the binary image of the motion region, an image slice index, and a ratio of white connected region in multiple sub-regions of the binary image of the motion region.

As a specific implementation mode, the predetermined image slice time series may be determined using a machine learning method, for example, using a support vector machine (SVM) classifier or any other appropriate classifier. In an embodiment, a classifier is trained with a sample set consisting of features extracted from the motion region of each image slice time series in the three-dimensional image time series and the predetermined image slice time series in the three-dimensional image time series is determined by using the trained classifier. By the classification method using the aforementioned features, the predetermined image slice time series can be determined conveniently and accurately in the three-dimensional image time series.

In a three-dimensional image time series, there may be some image slice time series which are beyond the real range of the moving object. The contours of the moving object extracted from such image slice time series are false and, if being used, will undermine the accuracy of subsequent parameter calculation for the moving object.

In an embodiment of the present invention, before acquiring the contour of a moving object, such image slice time series as mentioned above are determined and not subjected to the acquiring of the contour of the moving object or are directly deleted, so as to not undermine the accuracy of the subsequent parameter calculation. According to this embodiment, after the motion region of each image slice time series is detected and before the motion regions of the other image slice time series are adjusted by taking the motion region of the predetermined image slice time series as a reference, two image slice time series respectively corresponding to the two ends of the moving object are determined using at least one of the following features extracted from the motion region of each image slice time series: an average pixel value, a ratio of white connected region in a binary image of the motion region, an image slice index, and a ratio of white connected region in a plurality of sub-regions of a binary image of the motion region.

After the two image slice time series respectively corresponding to the two ends of the moving object are determined, in the following process of acquiring the contour of the moving object in each image slice, only the contours of the moving object in the image slices of the image slice time series between these two image slice time series are acquired. The two image slice time series corresponding to two ends of the moving object and the image slice time series outside the two image slice time series may be directly removed from the three-dimensional image time series.

Similarly, the two image slice time series corresponding to the two ends of the moving object can be determined using a machine learning method, for example, using an SVM classifier or any other appropriate classifier. In an embodiment, classifiers respectively for the two ends of the moving object are trained with a sample set consisting of the above feature(s) extracted from the motion region of each image slice time series in the three-dimensional image time series, and the two image slice time series corresponding to the two ends of the moving object in the three-dimensional image time series are determined using the trained two classifiers.

For a three-dimensional image time series acquired by an MRI device in the short axis direction of a heart, when the left ventricle is taken as the moving object, the two image slice time series corresponding to the two ends of the moving object refer to the image slice time series of the base part and the image slice time series of the apex part respectively.

FIG. 5 is a schematic flow chart illustrating the correcting of a contour of a moving object based on motion trend information of the moving object according to an embodiment of the present invention.

In step S510, the motion trend information of the moving object in each image slice time series is determined. It should be appreciated that a variation trend of the contour of the moving object may be used to represent the motion trend of the moving object. For instance, the variation trend of at least one of the features, such as radius, perimeter or area, of the contour of the moving object may be used to represent the motion trend of the moving object.

In step S520, a similarity between the motion trend information of the moving object in each image slice time series and reference motion trend information of the moving object is calculated. Here, the reference motion trend information of the moving object may be determined in advance. As an example but not a limitation, the reference motion trend information of the moving object may be average motion trend information of the moving object in the image slice time series or motion trend information of the moving object in an image slice time series that is predetermined as a template.

The similarity may be calculated using any appropriate existing similarity calculation method. As an example but not a limitation, the similarity may be calculated using a normalized cross correlation (NCC) algorithm. In order to facilitate understanding, a formula of the NCC algorithm (it is apparent that various mathematical transformations can be made to the formula) is presented below:

$$\rho(i, t) = \frac{\sum_{n=0}^{N} ((I_{i,n} - \bar{I}_i)(I_{t,n} - \bar{I}_t))}{\sqrt{\sum_{n=0}^{N} (I_{i,n} - \bar{I}_i)^2 \sum_{n=0}^{N} (I_{t,n} - \bar{I}_t)^2}} \quad \text{(Formula 1)}$$

In this formula, i represents an index of an image slice time series, the similarity of which is to be calculated, in the three-dimensional image time series, t represents an index of an image slice time series, which is predetermined as a template, in the three-dimensional image time series, N represents the number of the phases of an image slice time series (that is, the number of the acquisition time points corresponding to the image slices in an image slice time series, and the number equals to the number of the image slices of the image slice time series), $I_{i,n}$ represents the area (or another feature, such as perimeter or radius) of the moving object in an image slice corresponding to the $n^{th}$ phase of the $i^{th}$ image slice time series, $\bar{I}_i$ represents the average value of the areas (or another feature, such as perimeter or radius) of the moving object in all image slices of the $i^{th}$ image slice time series, and $\rho(i,t)$ represents the similarity between the motion trend information of the moving object in the $i^{th}$ image slice time series and the motion trend information (the reference motion trend information) of the moving object in the image slice time series t that is predetermined as a template.

In the case where the reference motion trend information of the moving object is the motion trend information of the moving object in the image slice time series that is predetermined as a template, $I_{t,n}$ represents the area (or another feature such as perimeter or radius) of the moving object in an image slice corresponding to the $n^{th}$ phase of the image slice time series that is predetermined as a template, and $\bar{I}_t$ represents the average value of the areas (or another feature such as perimeter or radius) of the moving object in all image slices of the image slice time series that is predetermined as a template.

In the case where the reference motion trend information of the moving object is the average motion trend information of the moving object in all image slice time series, $I_{t,n}$ represents the average value of the areas (or another feature, such as perimeter or radius) of the moving object in the image slices corresponding to the $n^{th}$ phase of the respective image slice time series, and $\bar{I}_t$ represents the average value of the areas (or another feature, such as perimeter or radius) of the moving object in all image slices of the respective image slice time series.

Additionally, preferably, in the case where the reference motion trend information of the moving object refers to the average motion trend information of the moving object in all the image slice time series, $I_{t,n}$ and $\bar{I}_t$ may be calculated according to the above description after the values of the feature (area, perimeter or radius) of the moving object in multiple image slices of each image slice time series are normalized. That is, $I_{t,n}$ may represent the average value of the normalized areas (or another feature, such as perimeter or radius) of the moving object in the image slices corresponding to the $n^{th}$ phase of the respective image slice time series, and $\bar{I}_t$ represents the average value of the normalized areas (or another feature, such as perimeter or radius) of the moving object in all image slices in the respective image slice time series.

In step S530, it is determined whether the similarity between the motion trend information of the moving object in the $i^{th}$ image slice time series and the reference motion trend information is lower than a predetermined threshold. If the similarity between the motion trend information of the moving object in the $i^{th}$ image slice time series and the reference motion trend information is lower than the predetermined threshold, which indicates that the contours acquired in the $i^{th}$ image slice time series may have errors and need to be corrected, the process proceeds to step S540; otherwise, the flow directly proceeds to step S550.

In step S540, the contours of the moving object in the $i^{th}$ image slice time series are corrected. According to an embodiment of the present invention, the contours of the moving object in the image slices in the $i^{th}$ image slice time series may be corrected using the contours of the moving object in the image slices of an image slice time series adjacent to the $i^{th}$ image slice time series.

In addition, if after the correction, the similarity between the motion trend information of the moving object in the $i^{th}$ image slice time series and the reference motion trend information is still lower than the predetermined threshold, which indicates that the corrected contours in the $i^{th}$ image slice time series still have errors, then the $i^{th}$ image slice time series may be removed from the three-dimensional image time series so as to avoid an undesirable influence on the subsequent processing.

In step S550, it is determined whether all the image slice time series have been subjected to the foregoing processing. If all image slice time series have been subjected to the foregoing processing, then the process is ended; otherwise, the process returns to step S520 to continue to calculate the similarity for a next image slice time series in the three-dimensional image time series.

In order to facilitate understanding, FIG. 6 shows an example of motion trends of a moving object in a plurality of image slice time series and similarities between the motion trends of the moving object and a reference motion trend. In this example, a variation trend of the area of the contour of the moving object is taken as a motion trend of the moving object. The S0, S1, . . . , S8 in the horizontal coordinate represent the reference signs of the image slice time series in spatial location. The vertical coordinate represents the area of the contour of the moving object. The multiple vertical lines at the reference sign of an image slice time series respectively represent the areas of the contour of the moving object in multiple image slices of the image slice time series. The variation trend of these vertical lines can reflect the motion trend of the moving object in the image slice time series. In this example, the motion trend of the moving object in the image slice time series S5 is taken as a reference motion trend. In addition, what shown below the horizontal coordinate is the similarity between the motion trend of the moving object in each image slice time series and the reference motion trend, which is calculated using the NCC method. It can be seen from FIG. 6 that the motion trends of the moving object in image slice time series S7 and S8 are significantly different from the reference motion trend. Accordingly, the similarities calculated for S7 and S8 are also low.

In order to facilitate understanding, FIG. 7 shows an example of the correcting of contours of a moving object in an image slice time series. In this example, the image slice time series S7 is a schematic diagram of an image slice time series in a three-dimensional image time series acquired by an MRI device in the short axis direction of a heart. In the example of FIG. 7, the left ventricle is taken as the moving object. In FIG. 7, the binary image in the second row shows uncorrected contours of the left ventricle in the image slice time series S7. It can be seen that before being corrected, the contours of the left ventricle in some image slices of the series S7 are greatly different from the real contour of the left ventricle. It can be determined by the foregoing similarity calculation that the contours of left ventricle in the series S7 need to be corrected. In FIG. 7, the binary images in the third row show uncorrected contours of the left ventricle in an image slice time series S6. The image slice time series S6 is an image slice time series adjacent to the image slice time series S7. The contours in the series S7 are corrected using the contours in the series S6 to obtain corrected contours in the series S7, as shown by the binary images in the fourth row of FIG. 7. After being corrected, the contours of the left ventricle in the series S7 are substantially approximate to the real contour of the left ventricle.

<2. A Left Ventricle Image Segmentation Method>

A left ventricle image segmentation method according to embodiments of the present invention is described below with reference to FIG. 8-13. The left ventricle image segmentation method according to the embodiments of the present invention is configured to acquire contours of a left ventricle from a three-dimensional medical image time series. Typically, a contour of a left ventricle refers to a contour of an endocardium (endocardial contour) of the left ventricle. Preferably, the left ventricle image segmentation method according to the embodiments of the present invention may be also configured to extract a contour of an epicardium (epicardial contour) of the left ventricle so as to determine a myocardium by combining the extracted endocardial contour with the extracted epicardial contour. The three-dimensional medical image time series includes a plurality of three-dimensional images acquired respectively at a plurality of time points in a period including at least one cardiac cycle. Each of the three-dimensional images consists of a plurality of parallel two-dimensional image slices that are intersected with a long axis of the let ventricle, and the two-dimensional image slices located at the same location in the plurality of three-dimensional images form an image slice time series.

Figure 8:
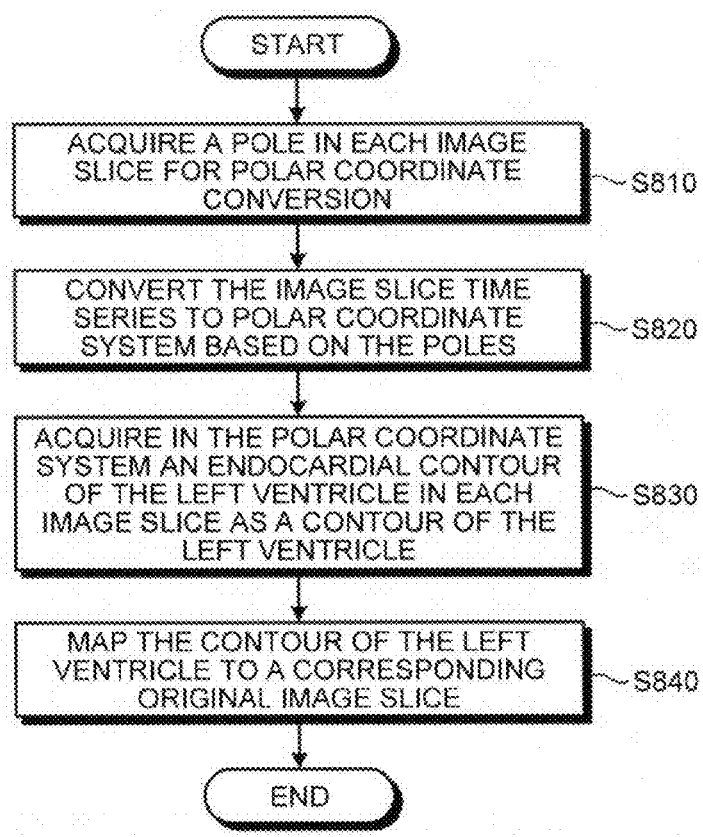
FIG. 8 is a schematic flow chart illustrating a left ventricle image segmentation method according to an embodiment of the present invention.

FIG. 8 is a schematic flow chart illustrating a left ventricle image segmentation method according to an embodiment of the present invention. In this embodiment, considering that the endocardial contour and the epicardial contour of the left ventricle are both curves, and the endocardial contour tends to be influenced by a papillary muscle and the epicardial contour is relatively blurry, the original image slice is converted into a polar coordinate system so that the contours of the endocardium and the epicardium can be extracted from the image slice more accurately.

Figure 9:
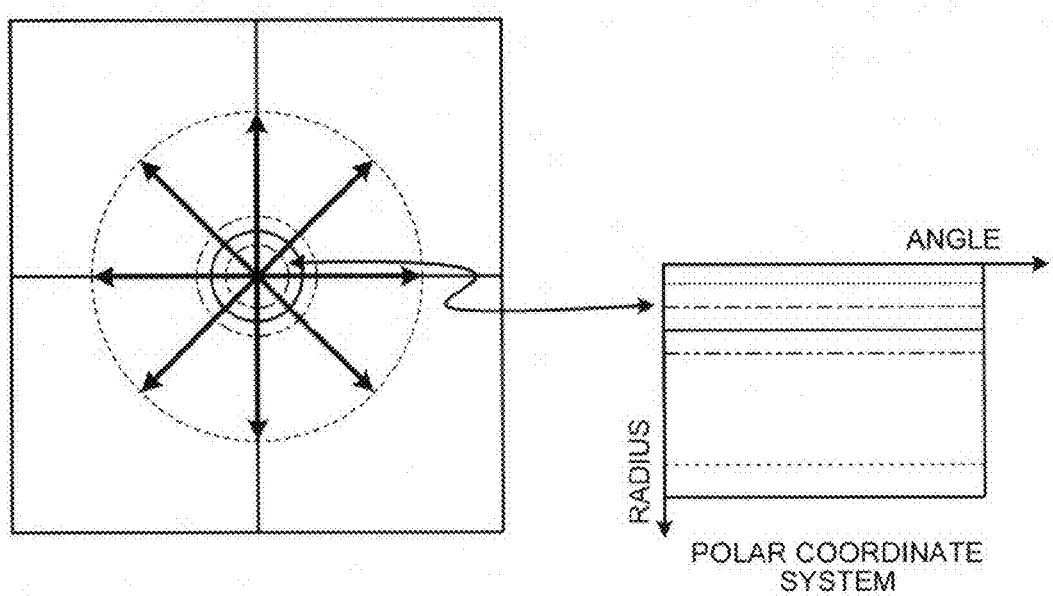
FIG. 9 is a schematic diagram illustrating a conversion relationship between a Euclidean coordinate system and a polar coordinate system.

In order to facilitate understanding, FIG. 9 shows a schematic diagram illustrating a conversion relationship between a Euclidean coordinate system and a polar coordinate system. In this figure, the origin of the Euclidean coordinate system corresponds to the pole of the polar coordinate system. The horizontal coordinate in the polar coordinate system represents the angle of a line connecting the origin with a point in the Euclidean coordinate system with respect to the positive direction of the horizontal axis of the Euclidean coordinate system, and the vertical coordinate in the polar coordinate system represents a distance between the origin and a point in the Euclidean coordinate system. After being converted to the polar coordinate system, the circles with different radiuses in the Euclidean coordinate system are presented as straight lines with different heights. On the other hand, after being converted to the Euclidean coordinate system, the straight lines with different heights in the polar coordinate system are presented as circles with different radiuses.

Returning to FIG. 8, in step S810, a pole for polar coordinate conversion is acquired in each image slice. The pole is typically the center of the contour of the left ventricle in the image slice. The pole may be marked manually or determined by an appropriate method in the art. According to an embodiment of the present invention, the left ventricle is taken as a moving object and a contour of the left ventricle is extracted by using the moving object contour extraction method described in foregoing embodiments from a three-dimensional medial image time series as an initial contour of the left ventricle, and the center of the initial contour of the left ventricle in an image slice is taken as the pole in the image slice.

In step S820, each image slice is converted to the polar coordinate system based on the pole in the image slice. In actual applications, in order into reduce the amount of calculation, only the motion region part in the image slice, rather than the whole image slice, is converted into the polar coordinate system.

In step S830, the endocardial contour of the left ventricle in each image slice is acquired in the polar coordinate system as the contour of the left ventricle in the image slice. The conversion to the polar coordinate system allows the detection of the endocardial contour and the epicardial contour to be easy and accurate. In the polar coordinate system, the contour of the endocardium is approximate to a straight line, and the extraction of the contour of the epicardium becomes easy as well. In addition, in the polar coordinate system, various types of information of a projection in the circumferential direction (the horizontal direction, the direction of the horizontal axis) such as brightness (typically represented with a pixel value) and edge can be used, which will be described later.

In step S840, the contour of the left ventricle acquired in the polar coordinate system is mapped to the corresponding original image slice. In the left ventricle, the endocardial contour acquired by a common method may be relative small due to the influence of the papillary muscle. Therefore, in the acquiring of the endocardial contour of the left ventricle, it is an important task to eliminate the influence of the papillary muscle and to contain the papillary muscle in a range defined by the endocardial contour so as to acquire a bigger and more accurate endocardial contour.

The endocardial contour of the left ventricle in each image slice can be acquired in the polar coordinate system using any appropriate existing method. It is described below a method for acquiring the endocardial contour of the left ventricle in each image slice in the polar coordinate system according to an embodiment of the present invention.

According to an embodiment of the present invention, in the case where a contour of a left ventricle is acquired from the three-dimensional medial image time series using the moving object contour extraction method described in a foregoing embodiment as the initial contour of the left ventricle, and a center of the initial contour of the left ventricle in an image slice is taken as the pole in the image slice, the endocardial contour of the left ventricle in each image slice can be acquired using the initial contour of the left ventricle in the image slice. Specifically, the initial contour of the left ventricle in each image slice can be converted to the polar coordinate system based on the pole in the image slice and then is smoothed in the polar coordinate system to obtain an endocardial contour in the image slice.

Figure 10A:
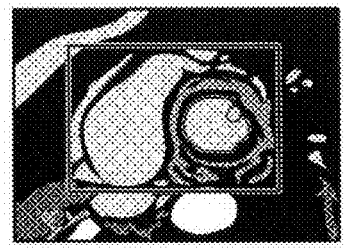
FIG. 10A and FIG. 10B are schematic diagrams illustrating the converting of an initial contour of a left ventricle into a polar coordinate system.
Figure 10B:

In order to facilitate understanding, FIG. 10a and FIG. 10b are schematic diagrams illustrating the conversion of an initial contour of a left ventricle to a polar coordinate system. FIG. 10a shows a schematic original image slice, in which the solid line frame in a substantially rectangular shape represents a motion region and the solid line in a substantially circular shape schematically shows the initial contour of the left ventricle. FIG. 10b is a schematic diagram illustrating an image obtained by converting the original image slice shown in FIG. 10a to a polar coordinate system by taking the center of the initial contour in the image slice as a pole. The initial contour of the left ventricle in a substantially circular shape in FIG. 10a is presented as a contour in a shape of approximate straight-line in the polar coordinate system. The protrusion on the contour represents the part where the papillary muscle is located. In this embodiment, the initial contour in an image slice can be smoothed in the polar coordinate system using any appropriate method to eliminate the influence of the papillary muscle and to acquire an endocardial contour in an approximate straight-line shape.

According to another embodiment of the present invention, a rough location of the endocardial contour is determined in the polar coordinate system using a circumferential directional projection of an image slice, and then the endocardial contour is acquired from an edge image of the image slice using a straight-line detection method. Specifically, edges in each image slice can be detected; a radius of the endocardial contour of the left ventricle in each image slice is acquired in the polar coordinate system using a circumferential directional projection (a horizontal projection) of a gray scale image of each image slice; and the endocardial contour of the left ventricle is acquired in the polar coordinate system from the edges nearby the radius of the endocardial contour of the left ventricle by using a straight-line detection method. It can be seen from the original image slice of the left ventricle that the grey scale of the myocardium of the left ventricle is smaller than that of the part inside the left ventricle. Accordingly, the location where a pixel value drops sharply in the circumferential directional projection of the gray scale image of the image slice can be taken as the location of the radius of the endocardial contour.

Figure 11:
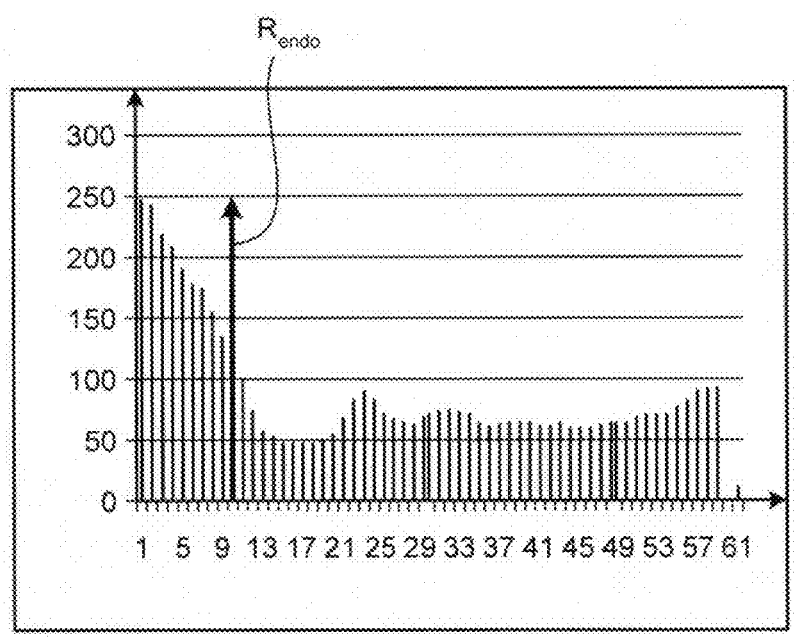
FIG. 11 is a schematic diagram illustrating a circumferential directional projection of a gray scale image of an image slice in a polar coordinate system.

In order to facilitate understanding, FIG. 11 shows a schematic diagram illustrating a circumferential directional projection of a gray scale image of an image slice in a polar coordinate system. In FIG. 11, the horizontal coordinate represents a row in a gray scale image of an image slice, and the vertical coordinate represents a sum or average of the pixel values in a row. An image slice is divided into rows by taking one or more pixels as a unit, depending on different demands on accuracy. As shown in FIG. 11, it is determined that the location where the sum or average of pixel values drops sharply is the location of the radius $R_{endo}$ of the endocardial contour.

According to another embodiment of the present invention, the two methods for acquiring an endocardial contour may be combined. Specifically, in this embodiment, edges in each image slice is detected; a first radius of the endocardial contour of the left ventricle in each image slice is acquired in the polar coordinate system using the circumferential directional projection of the gray scale image of each image slice; a second radius of the endocardial contour of the left ventricle in each image slice is acquired based on the initial contour of the left ventricle in each image slice; and the endocardial contour of the left ventricle is acquired in the polar coordinate system from the edges nearby an average location of the first and second radiuses of the endocardial contour of the left ventricle using a straight-line detection method. It should be appreciated that weighted averaging may be performed on the first and second radiuses according to application requirements.

In the foregoing embodiments of acquiring an endocardial contour, the straight-line detection method may be a Hough transformation method. In addition, in the process of smoothing the initial contour, the initial contour in an image slice may be fitted in the polar coordinate system using the Hough transformation method to obtain an endocardial contour containing the papillary muscle in the range of the endocardial contour. Compared with other methods, the Hough transformation method, when being used for fitting edge pixels (also referred to as edge points), can obtain a contour containing most of the edge points and eliminate the influence of the edge points such as the papillary muscle and noises. While in the other methods, generally edge pixels with small radiuses are also taken into account, thereby these methods tend to be influenced by the papillary muscle.

In addition to acquiring the endocardial contour of the left ventricle, an epicardial contour of the left ventricle may also be acquired in the left ventrical image segmentation method according to an embodiment of the present invention. The thickness of the myocardium can be determined according to the endocardial contour and the epicardial contour of the left ventricle.

According to an embodiment of the present invention, the edge pixels of an endocardial contour and the thickness of a myocardium can be determined using a circumferential directional projection of an image slice, so as to determine a rough location of the epicardial contour in a polar coordinate system, and then the epicardial contour can be acquired from an edge image of the image slice using a curve fitting method. Specifically, edges in each image pile can be detected; a radius of the endocardial contour of the left ventricle in each image slice is acquired in the polar coordinate system using a circumferential directional projection of a gray scale image of each image slice; a thickness of the myocardium of the left ventricle is determined in the polar coordinate system using a circumferential directional projection of an edge image of each image slice and the radius of the endocardial contour of the left ventricle in the image slice, thereby to acquire a radius of the epicardial contour of the left ventricle in each image slice; the epicardial contour of the left ventricle is acquired in the polar coordinate system from the edges nearby by the radius of the epicardial contour of the left ventricle using a curve fitting method; and the epicardial contour of the left ventricle is mapped to a corresponding original image slice.

Figure 12A:
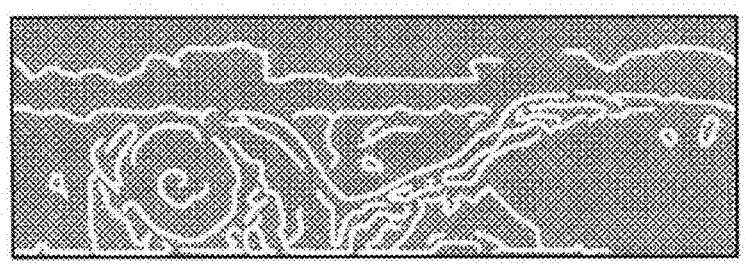
FIG. 12A is a schematic diagram illustrating an edge image of an image slice in a polar coordinate system.
Figure 12B:
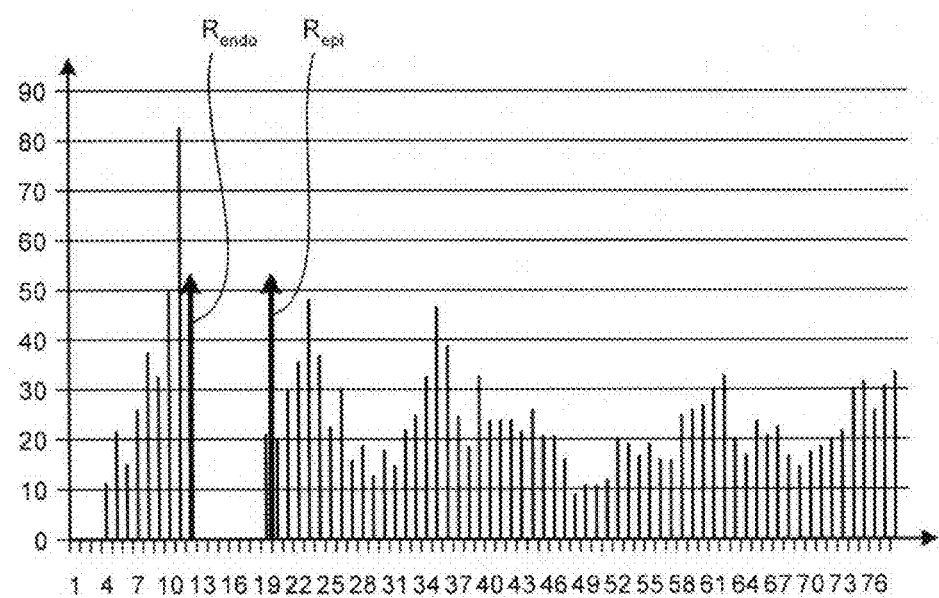
FIG. 12B is a schematic diagram illustrating a circumferential directional projection of the edge image shown in FIG. 12A.

In order to facilitate understanding, FIG. 12a shows a schematic diagram illustrating an edge image of an image slice in a polar coordinate system, and FIG. 12b shows a schematic diagram illustrating a circumferential directional projection the edge image shown in FIG. 12a. In FIG. 12b, the horizontal coordinate represents a row in the edge image of the image slice, and the vertical coordinate represents a sum or average of the pixel values in a row. An image slice may be divided into rows by taking one or more pixels as a unit, depending on different demands on accuracy. As shown in FIG. 12b, a location where the sum or average of pixel values drops sharply is determined as the location of the radius $R_{endo}$ of the endocardial contour. In the edge image, the myocardium part between the endocardial and epicardial contours substantially contains no edge. Therefore, there is a gap between the endocardial contour and the epicardial contour in the circumferential directional projection. Thus, as shown in FIG. 12b, the gap immediately next to the radius $R_{endo}$ of the endocardial contour is determined as the thickness of the myocardium between the endocardial contour and the epicardial contour, and the location behind the gap is determined as the location of the radius $R_{epi}$ of the epicardial contour.

Figure 13A:
FIG. 13A is a schematic diagram illustrating contours of an endocardium and an epicardium acquired in a polar coordinate system.
Figure 13B:
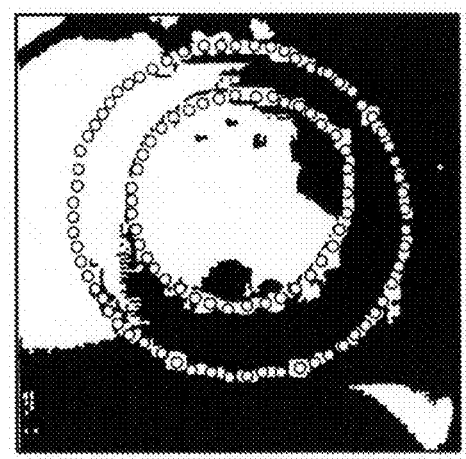
FIG. 13B is a schematic diagram illustrating the converting of the contours of the endocardium and the epicardium acquired in FIG. 13A into an original image slice.

In order to facilitate understanding, FIG. 13a shows a schematic diagram illustrating an endocardial contour and an epicardial contour acquired in a polar coordinate system according to the foregoing embodiments. In FIG. 13a, the upper contour line represents an endocardial contour, and the lower contour line represents an epicardial contour. FIG. 13b shows a schematic diagram illustrating conversion of the endocardial and epicardial contours acquired in FIG. 13a to a schematic original image slice. The endocardial contour (represented with a line formed of hollow dots) shown in FIG. 13b is relatively smooth and includes no protrusion, that is, the influence of the papillary muscle is eliminated.

In addition, according to an embodiment of the present invention, in the case where the moving object contour extraction method according to a foregoing embodiment is used to extract contours of a left ventricle from a three-dimensional medial image time series as initial contours of the left ventricle and a center of the initial contour of the left ventricle in each image slice is determined as a pole of the image slice, when recognizing the candidate regions of the moving object from the motion region of each image slice time series, the candidate regions of the left ventricle can be recognized from the motion region of each image slice time series according to multiple graphic features of the motion region of the image slice time series and an estimated central location of the left ventricle. As an example, the multiple graphic features of the motion region may be multiple graphic features of a connected region in the motion region being binarized.

In the process of recognizing candidate regions of the left ventricle automatically, due to that after the image slice is binarized and connected regions are marked in the image slice, the connected regions have various shapes and sizes, especially for the apex and the base, recognizing a candidate region of the left ventricle becomes difficult. In the apex part, the LV region is small and looks like noises if no other adjacent information can be acquired. In the base part, the LV region is always connected with a right ventricle (RV). In view of this, in this embodiment, a candidate region of the LV can be recognized using multiple graphic features of the connected region in a motion region. The features include, for example, all or part of the followings: area, circularity ratio, compactness, rectangularity, eccentricity and centroid distance variance. Here, the circularity ratio indicates how approximate the shape of a connected region is to a circle, the compactness indicates the ratio of the area of a connected region to the minimum border frame of the connected region, the rectangularity indicates the ratio of the width to the height or the height to the width of a connected region, the eccentricity indicates the ratio of the length of the primary axis to the secondary axis of a connected region, and the centroid distance variance indicates the variance of a distance from an edge point to the centroid of a connected region.

In addition of the graphic features of the connected region, the location of the LV is also used to allow the recognition of the LV to be more accurate. Here, a manually-noted LV central location or an estimated LV central location can be used. As a specific example, the central location of an LV can be estimated using an initial contour of the LV in an image slice time series that is predetermined as a template. Typically, the image slice time series that is predetermined as a template is the one located in the middle of all image slice time series, and the shape of the LV is more normal in such an image slice time series. In addition, the central line of the LV in a three-dimensional space can be fitted to assist the recognition. Candidate regions of the LV in the image slice time series that is predetermined as a template can be recognized using the graphic features of a connected region, and the center of each candidate region of the LV can be calculated as an estimated center of the LV.

Considering that the estimated central location of the LV is a relatively reliable feature, in an embodiment, in recognizing a candidate region of the left ventricle, a weight higher than those of the multiple graphic features is assigned to the estimated central location of the left ventricle.

<3. A Moving Object Contour Extraction Apparatus>

A moving object contour extraction apparatus according to embodiments of the present invention is described below with reference to FIG. 14-FIG. 17. The moving object contour extraction apparatus is configured to extract contours of a moving object which performs a deforming motion from a three-dimensional image time series. The three-dimensional image time series includes a plurality of three-dimensional images acquired at a plurality of time points. Each of the three-dimensional images consists of a plurality of parallel two-dimensional image slices. The two-dimensional image slices located at the same location in the three-dimensional images form an image slice time series. It should be appreciated that the moving object contour extraction apparatus according to the embodiments of the present invention may be used to extract contours of a moving object from various types of three-dimensional image time series. As an example but not a limitation, the three-dimensional image time series may be a medical image series formed by data on an examinee obtained by a medial diagnostic imaging device.

Figure 14:
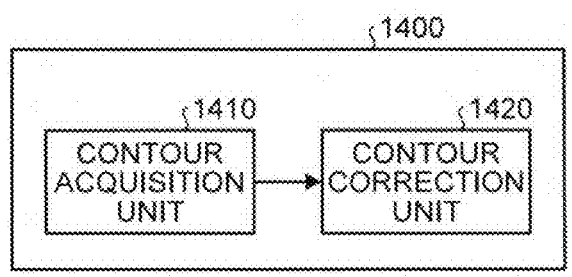
FIG. 14 is a schematic block diagram illustrating a moving object contour extraction apparatus according to an embodiment of the present invention.

FIG. 14 is a schematic block diagram illustrating a moving object contour extraction apparatus according to an embodiment of the present invention. As shown in FIG. 14, the moving object contour extraction apparatus 1400 includes a contour acquisition unit 1410 and a contour correction unit 1420. The contour acquisition unit 1410 is configured to acquire a contour of a moving object in each image slice. The contour correction unit 1420 is configured to correct the contours of the moving object in the image slices in at least one image slice time series based on motion trend information of the moving object in each of a plurality of image slice time series.

Figure 15:
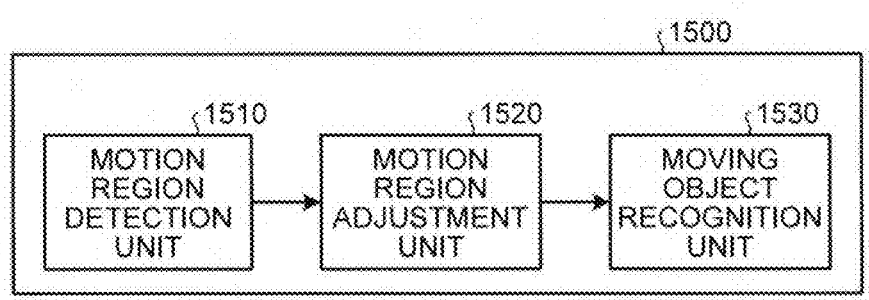
FIG. 15 is a schematic block diagram illustrating a contour acquisition unit according to an embodiment of the present invention.

Here, the contour of the moving object may be acquired by various existing methods. As an example, FIG. 15 shows a schematic block diagram illustrating a contour acquisition unit according to an embodiment of the present invention. As shown in FIG. 15, a contour acquisition unit 1500 includes a motion region detection unit 1510, a motion region adjustment unit 1520 and a moving object recognition unit 1530. The motion region detection unit 1510 is configured to detect a motion region of each image slice time series based on variations of the values of pixels in the image slice time series over time. The motion region adjustment unit 1520 is configured to adjust the motion regions of other image slice time series in the three-dimensional image time series than a predetermined image slice time series by taking the motion region of the predetermined image slice time series as a reference. Specifically, the motion region adjustment unit 1520 may adjust a motion region using the method described in step S220 shown in FIG. 2. The moving object recognition unit 1530 is configured to recognize candidate regions of the moving object from the motion regions of each image slice time series and take contours of the candidate regions as the contours of the moving object.

Figure 16:
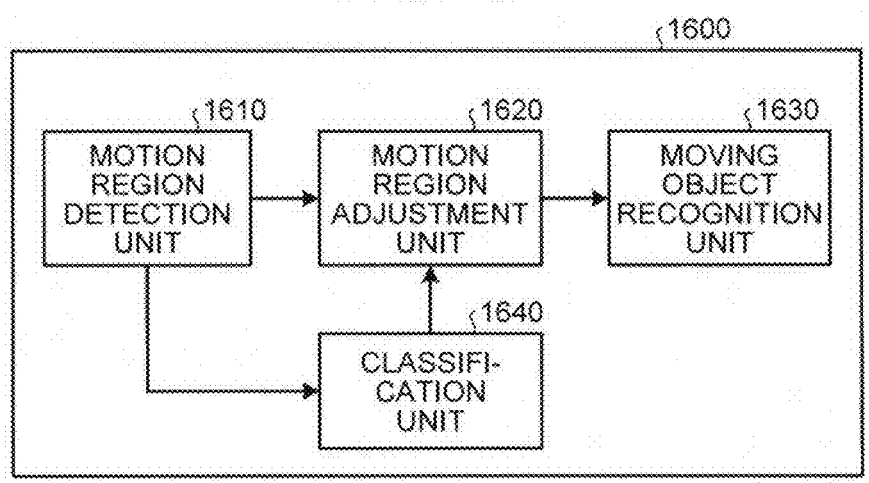
FIG. 16 is a schematic block diagram illustrating a contour acquisition unit according to another embodiment of the present invention.

According to an embodiment of the present invention, the predetermined image slice time series to be used in the motion region adjustment unit 1620 can be determined using the features extracted from the motion region of each image slice time series. FIG. 16 is a schematic block diagram illustrating the contour acquisition unit according to this embodiment. As shown in FIG. 16, a contour acquisition unit 1600 includes a motion region detection unit 1610, a motion region adjustment unit 1620, a moving object recognition unit 1630 and a classification unit 1640.

The motion region detection unit 1610, the motion region adjustment unit 1620 and the moving object recognition unit 1630 are substantially identical to the motion region detection unit 1510, the motion region adjustment unit 1520 and the moving object recognition unit 1530 included in the contour acquisition unit 1500 shown in FIG. 15, and thus will not be described repeatedly herein.

The classification unit 1640 is configured to determine the predetermined image slice time series to be used in the motion region adjustment unit 1620 using at least one of the following features extracted from the motion region of each image slice time series: an average pixel value, a ratio of white connected region in a binary image of the motion region, an image slice index, and a ratio of white connected region in a plurality of sub-regions of a binary image of the motion region. As a specific implementation mode, the classification unit 1640 may determine the predetermined image slice time series using the machine learning method described in the forgoing embodiments of a moving object contour extraction method.

According to another embodiment of the present invention, a contour acquisition unit has a substantially identical structure with the contour acquisition unit 1600 shown in FIG. 16 except that a classification unit may be configured to determine two image slice time series respectively corresponding to two ends of the moving object using at least one of the following features extracted from the motion region of each image slice time series: an average pixel value, a ratio of white connected region in a binary image of the motion region, an image slice index, and a ratio of white connected region in a plurality of sub-regions of a binary image of the motion region. In this embodiment, the contour acquisition unit can acquire the contours of the moving object in the image slices of the image slice time series between the two image slice time series, rather than acquiring the contours of the moving object for all image slice time series.

Figure 17:
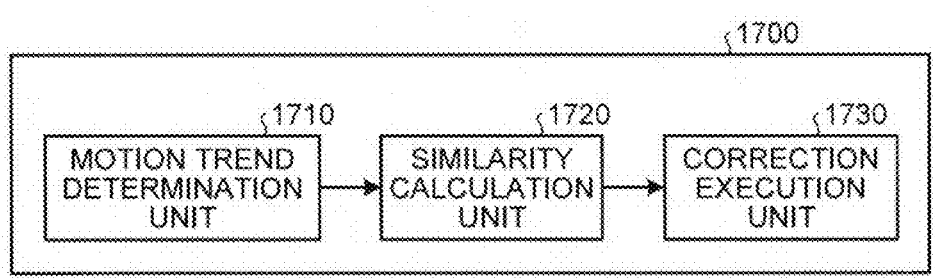
FIG. 17 is a schematic block diagram illustrating a contour correction unit according to an embodiment of the present invention.

After the contours of the moving object are acquired, the acquired contours of the moving object are corrected based on motion trend information of the moving object. FIG. 17 is a schematic block diagram illustrating a contour correction unit according to an embodiment of the present invention. As shown in FIG. 17, a contour correction unit 1700 includes a motion trend determination unit 1710, a similarity calculation unit 1720 and a correction execution unit 1730.

The motion trend determination unit 1710 is configured to determine the motion trend information of the moving object in each image slice time series.

The similarity calculation unit 1720 is configure to calculate a similarity between the motion trend information of the moving object in each image slice time series and reference motion trend information of the moving object. According to an embodiment of the present invention, the similarity calculation unit 1720 is configured to calculate average motion trend information of the moving object in all image slice time series as the reference motion trend information of the moving object, or to take motion trend information of the moving object in the mage slice time series that is predetermined as a template as the reference motion trend information of the moving object. In addition, the similarity calculation unit 1720 may calculate the similarity using the similarity calculation method described in step S520 shown in FIG. 5, such as the normalized cross correlation algorithm.

The correction execution unit 1730 is configured to correct the contours of the moving object in the image slices in a certain image slice time series if the similarity between the motion trend information of the moving object in the certain image slice time series and the reference motion trend information is lower than a predetermined threshold. According to an embodiment of the present invention, the contours of the moving object in the image slices in the certain image slice time series may be corrected with the contours of the moving object in the image slices in an image slice time series adjacent to the certain image slice time series. According to another embodiment of the present invention, the correction execution unit 1730 removes the certain image slice time series from the three-dimensional image time series if the similarity between the motion trend information of the moving object in the image slices in the certain image slice time series and the reference motion trend information is still lower than the predetermined threshold after the correction.

More detailed operations of each component in the moving objection contour extraction apparatus can be understood by reference to the above description of the moving objection contour extraction method according to the embodiments of the present invention and therefore are not described repeatedly here.

The moving objection contour extraction apparatus according to the embodiments of the present invention utilizes the motion trend of the moving object to correct the contours of the moving object so that the deformation of the moving object is turned into a beneficial factor for facilitating determining and removing error contours. In addition, by taking the motion region of the predetermined image slice time series which suffers the least interference as a reference to adjust the motion regions of the other image slice time series, the interference in the other image slice time series may be eliminated. Further, by determining the image slice time series in the three-dimensional image time series corresponding to two ends of the moving object, there is no need to extract the contours from the image slice time series outside the two ends of the moving object, thus reducing the amount of calculation and avoiding an undesired influence on the subsequent processing. In addition, the image slice time series in the three-dimensional time series corresponding to the two ends of the moving object can be accurately determined based on at least one feature of the moving region using a machine learning method such as an SVM classifier.

<4. A Left Ventricle Image Segmentation Apparatus>

A left ventricle image segmentation apparatus according to embodiments of the present invention is described below with reference to FIG. 18 to FIG. 21. The left ventricle image segmentation apparatus is configured to acquire contours of a left ventricle from a three-dimensional medical image time series. The three-dimensional medical image time series includes a plurality of three-dimensional images acquired at a plurality of time points in a period including at least one cardiac cycle. Each of the three-dimensional images consists of a plurality of parallel two-dimensional image slices that are intersected with a long axis of the left ventricle, and the two-dimensional image slices located at the same location in the three-dimensional images form an image slice time series.

Figure 18:
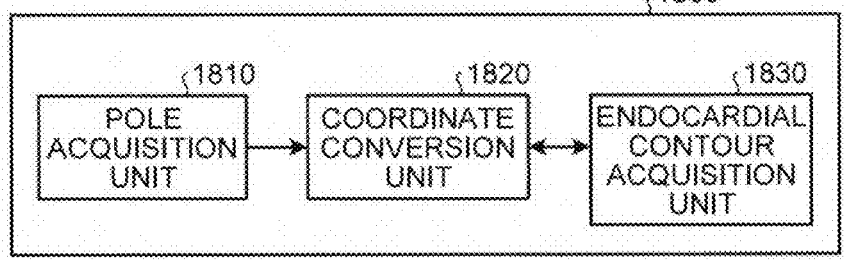
FIG. 18 is a schematic block diagram illustrating a left ventricle image segmentation apparatus according to an embodiment of the present invention.

FIG. 18 is a schematic block diagram illustrating a left ventricle image segmentation apparatus according to an embodiment of the present invention. As shown in FIG. 18, the left ventricle image segmentation apparatus 1800 includes a pole acquisition unit 1810, a coordinate conversion unit 1820 and an endocardial contour acquisition unit 1830. The pole acquisition unit 1810 is configured to acquire a pole in each image slice for polar coordinate conversion. The coordinate conversion unit 1820 is configured to convert each image slice into a polar coordinate system based on the pole in the image slice, and to map a contour of the left ventricle acquired by the endocardial contour acquisition unit 1830 to a corresponding original image slice. The endocardial contour acquisition unit 1830 is configured to acquire, in the polar coordinate system, an endocardial contour of the left ventricle in each image slice as the contour of the left ventricle in the image slice.

Figure 19:
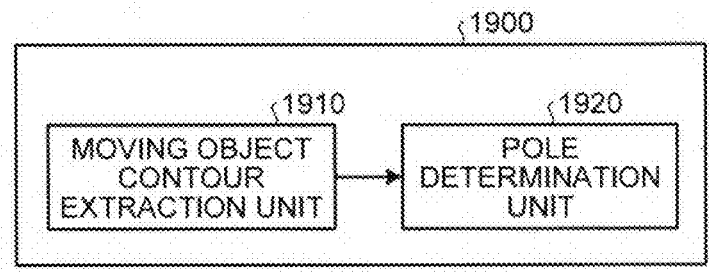
FIG. 19 is a schematic block diagram illustrating a pole acquisition unit according to an embodiment of the present invention.

The pole may be marked manually or determined by an appropriate method in the art. FIG. 19 is a schematic block diagram illustrating a pole acquisition unit according to an embodiment of the present invention. In FIG. 19, the pole acquisition unit 1900 includes a moving object contour extraction unit 1910 and a pole determination unit 1920. The moving object contour extraction unit 1910 is configured to extract contours of the left ventricle from the three-dimensional image time series as initial contours of the left ventricle. The moving object contour extraction unit 1910 may be implemented by the moving object contour extraction apparatus according to an embodiment of the present invention, taking the left ventricle as the moving object. The pole determination unit 1920 is configured to determine a center of the initial contour of the left ventricle in each image slice as the pole in the image slice.

The endocardial contour acquisition unit 1830 can acquire the endocardial contour of the left ventricle in each image slice in the polar coordinate system using any appropriate existing method.

According to an embodiment of the present invention, the coordinate conversion unit 1820 is further configured to convert the initial contour of the left ventricle in each image slice that is acquired by the moving object contour extraction unit 1910 of the pole acquisition unit 1900 to the polar coordinate system based on the pole in each image slice. The endocardial contour acquisition unit 1830 is further configured to smooth the initial contour in each image slice in the polar coordinate system to acquire the endocardial contour in each image slice. For instance, the endocardial contour acquisition unit 1830 may smooth the initial contour of the left ventricle in each image slice using a Hough transformation method. Thus, the final endocardial contour can be acquired based on the initial contour of the left ventricle acquired by the moving object contour extraction unit 1910.

Figure 20:
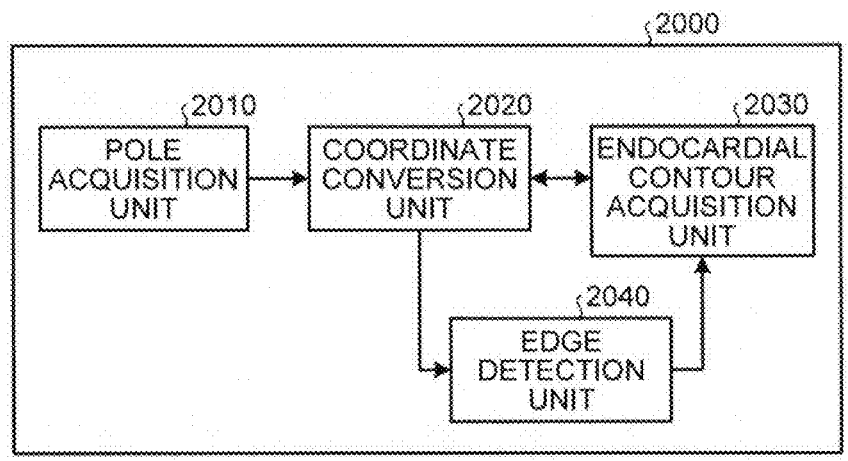
FIG. 20 is a schematic block diagram illustrating a left ventricle image segmentation apparatus according to another embodiment of the present invention.

According to another embodiment of the present invention, the endocardial contour acquisition unit 1830 may determine a rough location of the endocardial contour in the polar coordinate system using a circumferential directional projection of an image slice, and then acquire the endocardial contour from an edge image of the image slice using a straight-line detection method. FIG. 20 is a schematic block diagram illustrating a left ventricle image segmentation apparatus according to another embodiment of the present invention. As shown in FIG. 20, the left ventricle image segmentation apparatus 2000 includes a pole acquisition unit 2010, a coordinate conversion unit 2020, an endocardial contour acquisition unit 2030 and an edge detection unit 2040. The pole acquisition unit 2010 and the coordinate conversion unit 2020 are substantially identical to the pole acquisition unit 1810 and the coordinate conversion unit 1820 shown in FIG. 18. The edge detection unit 2040 is configured to detect edges in each image slice. It should be appreciated that the edge detection unit 2040 can detect the edges of each image slice in the polar coordinate system or in the Euclidean coordinate system, and then convert the edge image to the polar coordinate system. The endocardial contour acquisition unit 2030 is further configured based on the endocardial contour acquisition unit 1830 shown in the FIG. 18 to acquire, in the polar coordinate system, a radius of the endocardial contour of the left ventricle in each image slice using a circumferential directional projection of a gray scale image of each image slice; and to acquire the endocardial contour of the left ventricle from the edges nearby the radius of the endocardial contour of the left ventricle using a straight-line detection method.

According to another embodiment of the present invention, in the case where the moving object contour extraction unit 1910 is implemented by the moving object contour extraction apparatus according to an embodiment of the present invention, the endocardial contour acquisition unit 2030 may be further configured to acquire the endocardial contour in the following way: acquire, in the polar coordinate system, a first radius of the endocardial contour of the left ventricle in each image slice using a circumferential directional projection of a gray scale image of each image slice, acquire a second radius of the endocardial contour of the left ventricle in each image slice based on the initial contour of the left ventricle in each image slice, and acquire, in the polar coordinate system, the endocardial contour of the left ventricle from the edges nearby an average location of the first and second radiuses of the endocardial contour of the left ventricle using a straight-line detection method.

In the foregoing embodiments, the straight-line detection method used by the endocardial contour acquisition unit may be a Hough transformation method.

Figure 21:
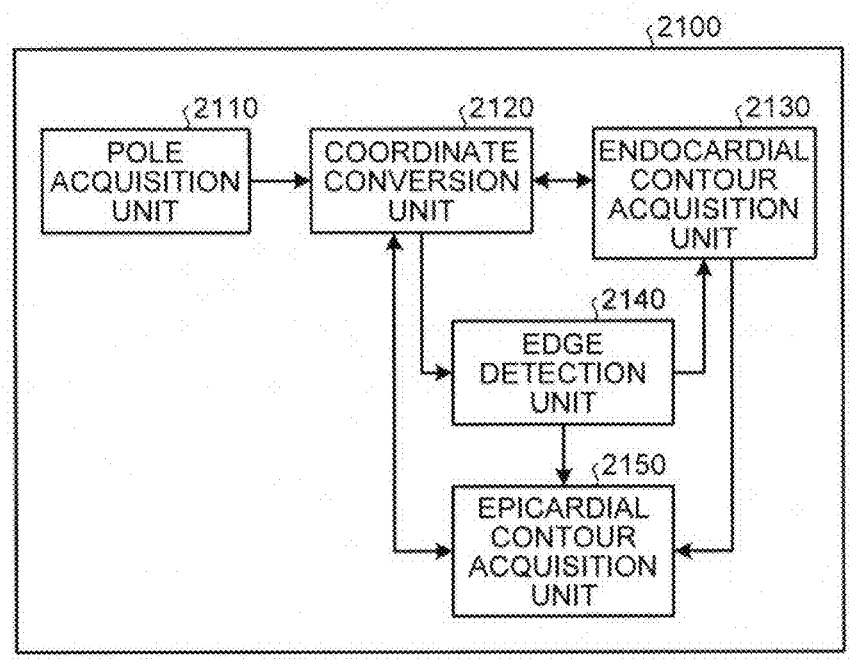
FIG. 21 is a schematic block diagram illustrating a left ventricle image segmentation apparatus according to still another embodiment of the present invention.

In order to further acquire the contour of the epicardium of the left ventricle, the left ventricle image segmentation apparatus according to an embodiment of the present invention may further comprise an epicardial contour acquisition unit. FIG. 21 shows a schematic block diagram illustrating a left ventricle image segmentation apparatus according to a further embodiment of the present invention. As shown in FIG. 21, the left ventricle image segmentation apparatus 2100 includes a pole acquisition unit 2110, a coordinate conversion unit 2120, an endocardial contour acquisition unit 2130, an edge detection unit 2140 and an epicardial contour acquisition unit 2150. The pole acquisition unit 2110, the coordinate conversion unit 2120 and the endocardial contour acquisition unit 2130 are substantially identical to the pole acquisition unit 1810, the coordinate conversion unit 1820 and the endocardial contour acquisition unit 1830 shown in FIG. 18. The edge detection unit 2140 is configured to detect edges in each image slice. The epicardial contour acquisition unit 2150 is configured to acquire an epicardial contour of the left ventricle. Specifically, the endocardial contour acquisition unit 2130 is further configured to acquire, in a polar coordinate system, a radius of an endocardial contour of the left ventricle in each image slice using a circumferential directional projection of a gray scale image of each image slice. The epicardial contour acquisition unit 2150 is configured to acquire, in the polar coordinate system, a radius of the epicardial contour of the left ventricle in each image slice using a circumferential directional projection of an edge image of each image slice and the radius of the endocardial contour of the left ventricle in the image slice, and to acquire, in the polar coordinate system, the epicardial contour of the left ventricle from the edges nearby the radius of the epicardial contour of the left ventricle using a curve fitting method. Further, in order to present the acquired epicardial contour, the coordinate conversion unit 2120 is further configured to map the epicardial contour of the left ventricle to a corresponding original image slice.

In addition, according to an embodiment of the present invention, when the moving object contour extraction unit in the pole acquisition unit of the left ventricle image segmentation apparatus is implemented by the moving object contour extraction apparatus according to an embodiment of the present invention, the moving object recognition unit in the moving object contour extraction apparatus recognizes the candidate regions of the left ventricle from the motion region of each image slice time series according to multiple graphic features of the motion region of the image slice time series and an estimated central location of the left ventricle. The estimated central location of the left ventricle may have a greater weight than the multiple graphic features.

More detailed operations on each component in the left ventricle image segmentation apparatus can be understood by reference to related description on the left ventricle image segmentation method and the moving objection contour extraction method according to the foregoing embodiments of the present invention and therefore are not repeated here.

In the left ventricle image segmentation apparatus according to embodiments of the present invention, an original image slice is converted to a polar coordinate system so that the endocardial contour which is originally a curve and blurry is presented as an approximate straight-line and relatively clear, thereby facilitating the more accurate segmentation of the left ventricle from an image slice. Further, the initial contour of the endocardium is smoothed in the polar coordinate system through a Hough conversion, or the contour of the endocardium is fitted from the edge pixel points of the endocardium using a straight-line detection method such as a Hough transformation method in the polar coordinate system, thus eliminating the influence caused by a papillary muscle. In addition, the rough locations of the endocardial and epicardial contours can be accurately determined using the projection of an image slice in the horizontal direction.

<5. A Computer Structure Capable of Implementing the Methods/Apparatuses in the Preset Disclosure>

As an example, the respective steps of the above-described moving object contour extraction method and the respective modules and/or units of the above-described moving object contour extraction apparatus may be implemented as software, firmware, hardware or the combination thereof in a medical diagnostic apparatus (e.g. X-ray diagnostic device, UL diagnostic device, CT device, MRI diagnostic device or PET device), and serve as a part of the medical diagnostic apparatus. As an example, the respective steps of the above-described left ventrical image segmentation method and the respective modules and/or units of the above-described left ventrical image segmentation apparatus may be implemented as software, firmware, hardware or the combination thereof in a medical diagnostic apparatus (e.g. X-ray diagnostic device, UL diagnostic device, CT device, MRI diagnostic device or PET device), and serve as a part of the medical diagnostic apparatus. The above-described methods and/or apparatuses may be implemented in an existing medical diagnostic device by making some modification on the sections of the existing medical diagnostic device. As another example, the respective steps of the above-described methods and the respective modules and/or units of the above-described apparatuses may be implemented as an apparatus separately from the above-described medical diagnostic apparatus. The specific means or approaches that may be used in configuring the modules and units in the foregoing apparatuses through software, firmware, hardware or any combination thereof are well known to those skilled in the art and therefore will not be repeatedly described.

As an example, the steps of the above-described methods and the modules and/or units of the above-described apparatuses may be implemented as software, firmware, hardware or any combination thereof. In the case where the steps of the above-described methods and the modules and/or units of the above-described apparatuses are implemented through software or firmware, a program constituting the software for implementing the above-described methods may be installed in a computer (e.g. the general computer 2200 shown in FIG. 22) with a dedicate hardware structure from a storage medium or a network, and the computer, when installed with various programs, is capable of perform various functions.

In FIG. 22, a central processing unit (i.e. CPU) 2201 executes various processes according to the programs stored in a read-only memory (ROM) 2202 or programs loaded to a random access memory (RAM) 2203 from a storage part 2208. Data needed by the CPU 2201 to execute the various processes are also stored in the RAM 2203 as required. The CPU 2201, the ROM 2202 and the RAM 2203 are connected with each other via a bus 2204. An input/output interface 2205 is also connected to the bus 2204.

The following parts are connected to the input/output (I/O) interface 2205: an input part 2206 (including a keyboard, a mouse and etc.), an output part 2207 (including a display such as a cathode-ray tube (CRT) or a liquid crystal display (LCD), and a speaker, etc.), the storage part 2208 (including a hard disk, etc.), and a communication part 2209 (including a network interface card such as an LAN card, a MODEM and etc.). The communication part 2209 executes communication processing via a network such as the Internet. A driver 2210 can also be connected to the input/output interface 2205 as required. A removable medium 2211 such as a magnetic disk, an optical disk, a magneto-optical disk or a semiconductor memory can be mounted on the driver 2210 as required, such that the computer program read out therefrom is installed into the storage part 2208 as required.

In the case that the above series of processes are implemented by software, a program constituting the software is installed from a network such as the Internet or from a storage medium such as the removable medium 2211.

It is to be understood by those skilled in the art that such storage medium is not limited to the removable medium 2211 storing programs therein and distributing the programs to a user(s) dependently from a device. Examples of the removable medium 2211 include a magnetic disk (including a Floppy Disk (registered trademark)), an optical disk (including a Compact Disk-Read Only Memory (CD-ROM) and a Digital Versatile Disc (DVD)), a magneto-optical disk (including a Microdisk (MD) (registered trademark)) and a semiconductor memory. Alternatively, the storage medium can be the ROM 2202, a hard disk contained in the storage part 2208, etc., in which programs are stored and which is distributed to a user(s) along with a device the storage medium is contained in.

The present invention further provides a program product in which computer-readable instruction codes are stored. The instruction codes, when read and executed by a machine, can execute the methods according to the embodiments of the present invention.

Correspondingly, the storage medium for carrying the program product storing machine-readable instruction codes is also incorporated in the disclosure of the present invention. The storage medium includes, but is not limited to, a flexible disk, an optical disk, a magneto-optical disk, a storage card and a storage stick.

In the above description of the specific embodiments of the present invention, features described and/or illustrated with respect to one embodiment can be used in one or more other embodiments in an identical or similar manner, be combined with features in other embodiments, or replace features in other embodiments.

It should be emphasized that, the term "comprise/include", as used in the present description, refers to the presence of features, sections, steps or components, but does not exclude the presence or addition of one or more other features, sections, steps or components.

In the above embodiments and examples, the steps and/or units are represented with a reference sign consisting of numbers. It should be understood by those of ordinary skill of the art that the reference signs are merely intended to facilitate description and drawing depiction, but are not to be construed as indicating the orders of the steps and/or units nor a limitation on any other aspect.

Furthermore, the methods of the present invention are not limited to being executed in the temporal orders as described in the specification, but can also be executed in other temporal order, in parallel or separately. Therefore, the execution orders of the methods described in the present specification do not constitute limitation to the technical scope of the present invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A moving object contour extraction apparatus for extracting from a three-dimensional image time series contours of a moving object which performs a deforming motion, the three-dimensional image time series comprising a plurality of three-dimensional images acquired at a plurality of time points, each of the three-dimensional images consisting of a plurality of parallel two-dimensional image slices, and the two-dimensional image slices located at the same location in the plurality of three-dimensional images forming an image slice time series, the apparatus comprising:
a contour acquisition unit configured to acquire a contour of the moving object in each image slice; and
a contour correction unit configured to correct the contours of the moving object in the image slices of at least one image slice time series based on motion trend information of the moving object in each of a plurality of the image slice time series, the contour correction unit comprising:
a motion trend determination unit configured to determine motion trend information of the moving object in each image slice time series;
a similarity calculation unit configured to calculate a similarity between the motion trend information of the moving object in each image slice time series and reference motion trend information of the moving object; and
a correction execution unit configured to correct the contours of the moving object in the image slices of a certain image slice time series if the similarity between the motion trend information of the moving object in the certain image slice time series and the reference motion trend information is lower than a predetermined threshold.

2. The apparatus according to claim 1, wherein the similarity calculation unit is configured to calculate average motion trend information of the moving object in the plurality of image slice time series as the reference motion trend information of the moving object, or to take the motion trend information of the moving object in an image slice time series that is predetermined as a template as the reference motion trend information of the moving object.

3. The apparatus according to claim 1, wherein the similarity calculation unit is configured to calculate the similarity using a normalized cross correlation algorithm.

4. The apparatus according to claim 1, wherein the correction execution unit is configured to correct the contours of the moving object in the image slices of the certain image slice time series with the contours of the moving object in the image slices of an image slice time series adjacent to the certain image slice time series.

5. The apparatus according to claim 4, wherein the correction execution unit is further configured to remove the certain image slice time series from the three-dimensional image time series if after the correction, the similarity between the motion trend information of the moving object in the image slices of the certain image slice time series and the reference motion trend information is still lower than the predetermined threshold.

6. The apparatus according to claim 1, wherein the contour acquisition unit comprises:
a motion region detection unit configured to detect a motion region of each image slice time series based on variations of values of pixels in the image slice time series over time;
a motion region adjustment unit configured to adjust, by taking the motion region of a predetermined image slice time series in the three-dimensional image time series as a reference, the motion regions of the other image slice time series in the three-dimensional image time series; and
a moving object recognition unit configured to recognize candidate regions of the moving object from the motion region of each image slice time series and take contours of the candidate regions of the moving object as the contours of the moving object.

7. The apparatus according to claim 6, wherein the contour acquisition unit further comprises:
a classification unit configured to determine the predetermined image slice time series using at least one of the following features extracted from the motion region of each image slice time series: an average pixel value, a ratio of white connected region in a binary image of the motion region, an image slice index, and a ratio of white connected region in a plurality of sub-regions of a binary image of the motion region.

8. The apparatus according to claim 6, wherein the contour acquisition unit further comprises:
a classification unit configured to determine two image slice time series using at least one of the following features extracted from the motion region of each image slice time series: an average pixel value, a ratio of white connected region in a binary image of the motion region, an image slice index, and a ratio of white connected region in a plurality of sub-regions of a binary image of the motion region,
wherein the contour acquisition unit is configured to acquire the contours of the moving object in the image slices of the image slice time series located between the two image slice time series.

9. The apparatus according to claim 1, wherein the three-dimensional image time series is a medical image series formed by data obtained through a medical diagnosis apparatus.

10. A moving object contour extraction method for extracting from a three-dimensional image time series contours of a moving object which performs a deforming motion, the three-dimensional image time series comprising a plurality of three-dimensional images acquired at a plurality of time points, each of the three-dimensional images consisting of a plurality of parallel two-dimensional image slices, and the two-dimensional image slices located at the same location in the plurality of three-dimensional images forming an image slice time series, the method comprising:
acquiring a contour of the moving object in each image slice; and
correcting the contours of the moving object in the image slices of at least one image slice time series based on motion trend information of the moving object in each of a plurality of the image slice time series,
by determining motion trend information of the moving object in each image slice time series;
by calculating a similarity between the motion trend information of the moving object in each image slice time series and reference motion trend information of the moving object; and
by correcting the contours of the moving object in the image slices of a certain image slice time series if the similarity between the motion trend information of the moving object in the certain image slice time series and the reference motion trend information is lower than a predetermined threshold.

11. A moving object contour extraction apparatus for extracting from a three-dimensional image time series contours of a moving object which performs a deforming motion, the three-dimensional image time series comprising a plurality of three-dimensional images acquired at a plurality of time points, each of the three-dimensional images consisting of a plurality of parallel two-dimensional image slices, and the two-dimensional image slices located at the same location in the plurality of three-dimensional images forming an image slice time series, the apparatus comprising:
circuitry configured to
acquire a contour of the moving object in each image slice,
correct the contours of the moving object in the image slices of at least one image slice time series based on motion trend information of the moving object in each of a plurality of the image slice time series,
determine motion trend information of the moving object in each image slice time series,
calculate a similarity between the motion trend information of the moving object in each image slice time series and reference motion trend information of the moving object, and
correct the contours of the moving object in the image slices of a certain image slice time series if the similarity between the motion trend information of the moving object in the certain image slice time series and the reference motion trend information is lower than a predetermined threshold.

* * * * *